United States Patent
Matsubara

(10) Patent No.: US 10,139,335 B2
(45) Date of Patent: Nov. 27, 2018

(54) OBSERVATION IMAGE DETERMINATION DEVICE, METHOD, AND PROGRAM

(71) Applicant: FUJIFILM Corporation, Tokyo (JP)

(72) Inventor: Kenta Matsubara, Ashigarakami-gun (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 0 days.

(21) Appl. No.: 15/045,691

(22) Filed: Feb. 17, 2016

(65) Prior Publication Data

US 2016/0161394 A1    Jun. 9, 2016

Related U.S. Application Data

(63) Continuation of application No. PCT/JP2014/004207, filed on Aug. 18, 2014.

(30) Foreign Application Priority Data

Aug. 22, 2013   (JP) ................. 2013-172382

(51) Int. Cl.
*G06K 9/00* (2006.01)
*G01N 15/14* (2006.01)
(Continued)

(52) U.S. Cl.
CPC ......... *G01N 15/1463* (2013.01); *C12M 41/36* (2013.01); *C12Q 1/04* (2013.01);
(Continued)

(58) Field of Classification Search
None
See application file for complete search history.

(56) References Cited

U.S. PATENT DOCUMENTS

2004/0029213 A1* 2/2004 Callahan ............ G01N 15/1475
                                                          435/40.5
2006/0018514 A1* 1/2006 Bankhead ............ G01B 11/303
                                                          382/108
(Continued)

FOREIGN PATENT DOCUMENTS

JP     2004-229619 A    8/2004
JP     2009-44974 A     3/2009
(Continued)

OTHER PUBLICATIONS

International Search Report for PCT/JP2014/004207 dated Nov. 4, 2014.
(Continued)

*Primary Examiner* — Hadi Akhavannik
(74) *Attorney, Agent, or Firm* — Sughrue Mion, PLLC

(57) ABSTRACT

An observation image determination device includes an observation image acquisition unit that captures an image of an observation region including a stem cell to be cultured to acquire an observation image and a determination unit that determines whether a living body of a different type from the stem cell is included in the observation region. The determination unit determines whether the different type of living body is included in the observation region, on the basis of at least one of form information of an observation target and information about a change in the observation target over time which are acquired from the observation image.

17 Claims, 4 Drawing Sheets

(51) Int. Cl.
  *C12Q 1/04*    (2006.01)
  *C12M 1/34*    (2006.01)
  *G06K 9/62*    (2006.01)
  *G06T 7/00*    (2017.01)
  *G06T 7/20*    (2017.01)
  *H04N 5/232*   (2006.01)
  *H04N 5/235*   (2006.01)
  *G01N 15/00*   (2006.01)
  *G01N 15/10*   (2006.01)

(52) U.S. Cl.
  CPC ....... *G01N 15/1475* (2013.01); *G06K 9/6201* (2013.01); *G06T 7/0012* (2013.01); *G06T 7/20* (2013.01); *H04N 5/2353* (2013.01); *H04N 5/23296* (2013.01); *G01N 2015/0088* (2013.01); *G01N 2015/1006* (2013.01); *G01N 2015/1488* (2013.01); *G01N 2015/1493* (2013.01); *G01N 2015/1497* (2013.01); *G06K 2009/6213* (2013.01); *G06T 2207/30024* (2013.01)

(56) References Cited

U.S. PATENT DOCUMENTS

| | | | | |
|---|---|---|---|---|
| 2007/0285541 A1* | 12/2007 | Nakashiba | ........... | G06K 9/0004 348/272 |
| 2008/0176276 A1* | 7/2008 | Arai | ................... | G01N 33/5005 435/40.5 |
| 2008/0273786 A1* | 11/2008 | Komori | ................ | G02B 21/367 382/133 |
| 2009/0087075 A1* | 4/2009 | Kii | ......... | G02B 21/06 382/133 |
| 2010/0260422 A1* | 10/2010 | Ito | ......... | C12M 41/14 382/190 |
| 2011/0002525 A1* | 1/2011 | Mimura | ................ | C12M 23/48 382/133 |
| 2011/0298909 A1* | 12/2011 | Ando | ................... | H04N 5/2256 348/77 |
| 2012/0092478 A1 | 4/2012 | Honda et al. | | |

FOREIGN PATENT DOCUMENTS

| | | |
|---|---|---|
| JP | 2011-229411 A | 11/2011 |
| JP | 2011-229413 A | 11/2011 |
| JP | 2013-39113 A | 2/2013 |
| WO | 2007/136074 A1 | 11/2007 |
| WO | 2010/098105 A1 | 9/2010 |

OTHER PUBLICATIONS

Written Opinion for PCT/JP2014/004207 dated Nov. 4, 2014.
Communication dated Sep. 6, 2016, from the Japanese Patent Office in counterpart application No. 2013-172382.

* cited by examiner

OBSERVATION IMAGE DETERMINATION DEVICE, METHOD, AND PROGRAM

CROSS-REFERENCE TO RELATED APPLICATIONS

This application is a Continuation of PCT International Application No. PCT/JP2014/004207 filed on Aug. 18, 2014, which claims priority under 35 U.S.C. § 119(a) to Japanese Patent Application No. 2013-172382 filed on Aug. 22, 2013. Each of the above applications is hereby expressly incorporated by reference, in its entirety, into the present application.

BACKGROUND OF THE INVENTION

1. Field of the Invention

The present invention relates to an observation image determination device and method and a program which determine whether or not a different type of living body, other than a stem cell is included in an observation region, on the basis of an observation image obtained by capturing an image of the observation region including the stem cell.

2. Description of the Related Art

A stem cell, such as an ES cell or an iPS cell, has the capability to be differentiated to cells of various tissues and has drawn attention since it can be applied to, for example, regenerative medicine, the development of drugs, and the interpretation of disease.

The stem cell is seeded in a culture medium in a culture container which is provided in a cell culture device and is multiplied in the culture container. Stem cell colonies are grown while adjacent stem cell colonies are repeatedly combined with each other.

It is necessary to multiply the stem cell while maintaining the stem cell in an undifferentiated state, in order to improve differentiation efficiency when the stem cell is differentiated to a cell of a target tissue in the growth process of the stem cell.

SUMMARY OF THE INVENTION

In the growth process of the stem cell, it is also necessary to manage the stem cell such that the stem cell is not contaminated by, for example, bacteria, in addition to the necessity of multiplying the stem cell while maintaining the stem cell in an undifferentiated state, as described above. The stem cell contaminated by, for example, bacteria, is not available and should be discarded.

In the culture of general cells, an antibiotic, such as penicillin, is added and mixed with the culture medium in order to avoid the risk of the mixture of bacteria. However, in the culture of the stem cell, it is difficult to add and mix the antibiotic since the antibiotic affects the growth of the stem cell.

When a certain period of time has elapsed since the mixture of bacteria, the bacteria are in a fungal state. Therefore, it is difficult for non-experts to check the mixture of bacteria. When bacteria are multiplied, not only one culture container, but also other culture containers provided in the cell culture device are likely to be contaminated by the bacteria. Therefore, it is necessary to quickly detect the culture container having the bacteria mixed therein and to remove the culture container.

JP2004-229619A discloses a method which adds a sample to a culture medium and compares the intensity of fluorescence with a threshold value on the basis of the sample to determine whether or not microbes, such as bacteria, are present. However, in the method disclosed in Patent Document 1, it is necessary to add a sample according to the type of bacteria and it requires a lot of time and effort to add the sample. In addition, costs increase.

The invention has been made in view of the above-mentioned problems and an object of the invention is to provide an observation image determination device and method and a program which can quickly detect the mixture of a different type of living body, such as bacteria, without adding, for example, a sample.

According to an aspect of the invention, there is provided an observation image determination device including: an observation image acquisition unit that captures an image of an observation region including a stem cell to be cultured to acquire an observation image; and a determination unit that determines whether or not a living body of a different type from the stem cell is included in the observation region. The determination unit determines whether or not the different type of living body is included in the observation region, on the basis of at least one of form information of an observation target and information about a change in the observation target over time which are acquired from the observation image.

In the observation image determination device according to the above-mentioned aspect of the invention, the determination unit may acquire at least one of the size, shape, and frequency characteristics of the observation target as the form information.

When the observation target having a size equal to or less than a predetermined size threshold value is present, the determination unit may determine that the different type of living body is included in the observation region.

The determination unit may perform pattern matching between the shape of the observation target and a predetermined shape of the different type of living body to determine whether the different type of living body is included in the observation region.

The determination unit may compare the frequency characteristics of the observation target with predetermined frequency characteristics of the different type of living body to determine whether the different type of living body is included in the observation region.

The determination unit may acquire at least one of an amount of movement of the observation target and a multiplication rate of the observation target as the information about the change in the observation target over time.

When the amount of movement of the observation target is equal to or greater than a predetermined movement amount threshold value, the determination unit may determine that the different type of living body is included in the observation region.

When the multiplication rate of the observation target is equal to or greater than a predetermined multiplication rate threshold value, the determination unit may determine that the different type of living body is included in the observation region.

The observation image determination device according to the above-mentioned aspect of the invention may further include an imaging unit that captures the observation image. The imaging unit may perform switching between a first imaging interval when the observation image used to determine whether the different type of living body is included is captured and a second imaging interval when the observation image used to observe the stem cell is captured. The first imaging interval may be shorter than the second imaging interval.

The determination unit may output an end signal to the imaging unit when the determination of whether the different type of living body is included ends and the imaging unit may automatically switch the first imaging interval to the second imaging interval in response to the end signal.

The imaging unit may perform switching between a first magnification when the observation image used to determine whether the different type of living body is included is captured and a second magnification when the observation image used to observe the stem cell is captured. The first magnification may be higher than the second magnification.

The determination unit may output an end signal to the imaging unit when the determination of whether the different type of living body is included ends and the imaging unit may automatically switch the first magnification to the second magnification in response to the end signal.

The imaging unit may perform switching between a first exposure time when the observation image used to determine whether the different type of living body is included is captured and a second exposure time when the observation image used to observe the stem cell is captured. The first exposure time may be longer than the second exposure time.

The determination unit may output an end signal to the imaging unit when the determination of whether the different type of living body is included ends and the imaging unit may automatically switch the first exposure time to the second exposure time in response to the end signal.

The observation image determination device according to the above-mentioned aspect of the invention may further include an imaging unit that captures the observation image. The imaging unit may perform switching between a first amount of exposure when the observation image used to determine whether the different type of living body is included is captured and a second amount of exposure when the observation image used to observe the stem cell is captured. The second amount of exposure may be more than the first amount of exposure.

The determination unit may output an end signal to the imaging unit when the determination of whether the different type of living body is included ends and the imaging unit may automatically switch the first amount of exposure to the second amount of exposure in response to the end signal.

According to another aspect of the invention, there is provided an observation image determination method including: capturing an image of an observation region including a stem cell to be cultured to acquire an observation image; and determining whether a different type of living body is included in the observation region, on the basis of at least one of form information of an observation target and information about a change in the observation target over time which are acquired from the observation image.

According to another aspect of the invention, there is provided an observation image determination program that causes a computer to function as: an observation image acquisition unit that captures an image of an observation region including a stem cell to be cultured to acquire an observation image; and a determination unit that determines whether a living body of a different type from the stem cell is included in the observation region. The determination unit determines whether the different type of living body is included in the observation region, on the basis of at least one of form information of an observation target and information about a change in the observation target over time which are acquired from the observation image.

According to the observation image determination device and method and the program of the invention, an observation image obtained by capturing the image of the observation region including the stem cell is acquired, and it is determined whether a different type of living body is included in the observation region, on the basis of at least one of the form information of the observation target and the information about a change in the observation target over time which are acquired from the acquired observation image. Therefore, it is possible to quickly detect the mixture of a different type of living body, such as bacteria, without adding, for example, a sample.

DESCRIPTION OF THE PREFERRED EMBODIMENTS

Figure 1:
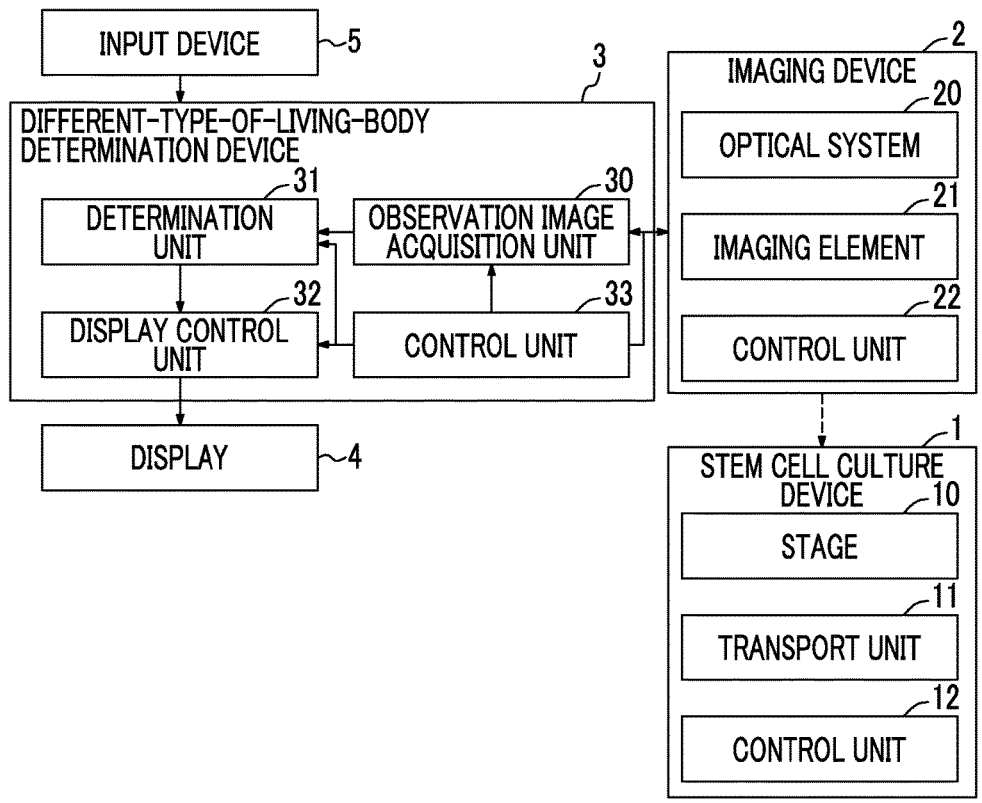
FIG. 1 is a block diagram schematically illustrating the structure of a stem cell culture observation system using an embodiment of an observation image determination device according to the invention.

Hereinafter, an embodiment of an observation image determination device and method and a program according to the invention will be described in detail with reference to the drawings. The invention is characterized in a method for determining whether different types of living bodies are included in an observation image which is a captured image of a stem cell. First, the overall structure of a stem cell culture observation system including the observation image determination device will be described. FIG. 1 is a block diagram schematically illustrating the structure of the stem cell culture observation system.

As illustrated in FIG. 1, the stem cell culture observation system includes a stem cell culture device 1, an imaging device 2, a different-type-of-living-body determination device 3, a display 4, and an input device 5. In this embodiment, the imaging device 2 and the different-type-of-living-body determination device 3 correspond to the observation image determination device.

The stem cell culture device 1 is used to culture stem cells. The stem cell culture device 1 includes a plurality of culture containers in which the stem cells to be cultured are seeded in a culture medium. The stem cell culture device 1 includes a stage 10, a transport unit 11, and a control unit 12.

The culture container of which the image is to be captured by the imaging device 2 is placed on the stage 10. The transport unit 11 selects the culture container of which the image is to be captured from a plurality of culture containers which are accommodated at predetermined positions in the stem cell culture device 1 and transports the selected culture container to the stage 10. The control unit 12 controls the overall operation of the stem cell culture device 1 and controls environmental conditions, such as temperature, humidity, and $CO_2$ concentration, in the cell stem culture device 1, in addition to the operation of the stage 10 or the transport unit 11. A known structure can be used to adjust the temperature, humidity, and $CO_2$ concentration.

The imaging device 2 captures an observation image of an observation region including the stem cell in the culture container placed on the stage 10. The imaging device 2 includes an optical system 20 which forms and captures the observation image, an imaging element 21 which converts the observation image formed by the optical system 20 into an electric signal and outputs the electric signal as an image signal, and a control unit 22 which controls the optical system 20 and the imaging element 21.

For example, a phase contrast microscope or a differential interference microscope can be used as the optical system 20. For example, a complementary metal-oxide semiconductor (CMOS) sensor or a charge-coupled device (CCD) sensor can be used as the imaging element 21.

The control unit 22 controls the overall operation of the imaging device 2. Particularly, in this embodiment, the control unit 22 controls the imaging interval of the observation image, the magnification of the optical system 20, the amount of exposure of illumination light, and an exposure time.

Specifically, in this embodiment, the different-type-of-living-body determination device 3 determines whether a different type of living body other than the stem cell is included in the observation region on the basis of the observation image. When it is determined that a different type of living body is not included in the observation region, the stem cell in the observation image is observed in detail. The control unit 22 performs switching between a first imaging interval when the observation image used to determine whether a different type of living body is included is captured, and a second imaging interval when the observation image used to observe the stem cell in detail is captured. The control unit 22 sets the first and second imaging intervals such that the first imaging interval is shorter than the second imaging interval. For example, the first imaging interval is set to 1 fps to 100 fps and the second imaging interval is set to one hour to one day or two days.

Since the first imaging interval is set to a relatively small value, it is possible to appropriately check the fast movement of a different type of living body, such as bacteria, for example, when the amount of movement of an observation target in the observation image, which will be described below, is acquired. In addition, since the imaging interval of the observation image for observing the stem cell is long, it is possible to perform exposure a plurality of times and to add a plurality of observation images, for example, when imaging is performed at an interval of one hour to one day or two days. Therefore, it is possible to obtain an observation image with a high S/N ratio. The plurality of exposure processes cause a substantial increase in the exposure time by a value corresponding to the plurality of exposure processes. The control unit 22 controls the imaging element 21 to switch the number of exposures.

In this embodiment, the number of exposures (exposure time) changes depending on a change in the first imaging interval and the second imaging interval. However, the number of exposures (exposure time) may not necessarily change, or only the imaging interval may be switched and the number of exposures (exposure time) may be constant.

For the switching between the imaging intervals, the control unit 22 may receive an end signal indicating that the determination of whether a different type of living body is included by the different-type-of-living-body determination device 3 has ended and may automatically switch the imaging interval on the basis of the end signal. Alternatively, when the determination ends, the user may input an instruction to switch the imaging interval, using the input device 5, and the control unit 22 may switch the imaging interval on the basis of the input instruction signal.

The control unit 22 performs switching between a first magnification when the observation image used to determine whether a different type of living body is included is captured and a second magnification when the observation image used to observe the stem cell in detail is captured. The control unit 22 sets the first and second magnifications such that the first magnification is higher than the second magnification. For example, a magnification of 10 to 40 may be set as the first magnification and a magnification of 4 to 20 may be set as the second magnification.

As such, since the first magnification is set to a relatively large value, it is possible to appropriately detect a different type of living body such as bacteria with a size of several hundreds of nanometers to several micrometers. In addition, as described above, the first magnification relatively increases to relatively narrow the observation region. Since a different type of living body, such as bacteria, is uniformly distributed in the culture container, it is possible to check the existence of a different type of living body only by observing a portion of the culture container. The second magnification relatively decreases to relatively widen the observation region. Therefore, it is possible to observe the entire stem cell colony and to appropriately determine the undifferentiation and differentiation of the stem cell.

For the switching between the magnifications, the control unit 22 may receive an end signal indicating that the determination of whether a different type of living body is included by the different-type-of-living-body determination device 3 has ended and may automatically switch the magnification on the basis of the end signal. Alternatively, when the determination ends, the user may input an instruction to switch the magnification, using the input device 5, and the control unit 22 may switch the magnification on the basis of the input instruction signal.

The control unit 22 performs switching between a first amount of exposure when the observation image used to determine whether a different type of living body is included is captured, and a second amount of exposure when the observation image used to observe the stem cell in detail is captured. In this case, the control unit 22 sets the first and second amounts of exposure such that the first amount of exposure is more than the second amount of exposure.

As described above, if the first magnification when the observation image for determining a different type of living body is captured is higher than the second magnification when the observation image for observing the stem cell is captured, the observation image for determining a different type of living body is optically dark. Therefore, as described above, it is preferable that the first amount of exposure when the observation image for determining a different type of living body is captured is relatively large.

Since the observation image for observing the stem cell is captured at the second magnification which is relatively low and is optically bright, the amount of exposure is the second amount of exposure which is relatively small. In addition, as described above, the observation image for observing the stem cell can be captured by for example, a plurality of exposure processes. Therefore, it is possible to improve the S/N ratio of the observation image.

For the switching between the amounts of exposure, the amount of illumination light from a light source provided in the optical system 20 may be switched, a diaphragm may be switched, a neutral density filter may be used, or a mechanical shutter time may be switched.

For the switching between the amounts of exposure, the control unit 22 may receive an end signal indicating that the determination of whether a different type of living body is included by the different-type-of-living-body determination device 3 has ended and may automatically switch the amount of exposure on the basis of the end signal. Alternatively, when the determination ends, the user may input an instruction to switch the amount of exposure, using the input device 5, and the control unit 22 may switch the amount of exposure on the basis of the input instruction signal.

An embodiment of an observation image determination program according to the invention is installed in a computer to implement the different-type-of-living-body determination device 3.

The different-type-of-living-body determination device 3 includes, for example, a central processing unit, a semiconductor memory, and a hard disk and an embodiment of the observation image determination program is installed in the hard disk. When the control unit 33 including a central processing unit executes the program, an observation image acquisition unit 30, a determination unit 31, and a display control unit 32 illustrated in FIG. 1 operate.

The observation image acquisition unit 30 acquires the observation image output from the imaging device 2 and stores the observation image. In addition, the observation image acquisition unit 30 outputs the acquired observation image to the determination unit 31 and the display control unit 32.

The determination unit 31 determines whether a living body of a different type from the stem cell is included in the observation region on the basis of the input observation image. The different type of living body is, for example, living bodies, such as bacteria which have an adverse effect on the culture of the stem cell.

Specifically, the determination unit 31 acquires at least one of form information about of an observation target and information about a change in the observation target over time from the input observation image and determines whether a different type of living body is included in the observation region, on the basis of the acquired form information or the acquired information about the change in the observation target over time.

The form information of the observation target includes, for example, the size, shape, and frequency characteristics of the observation target. The determination unit 31 acquires at least one of them and determines whether a different type of living body is included in the observation region.

For example, when the size of the observation target is acquired, a stem cell colony has a size of several hundreds of micrometers to several millimeters while a different type of living body, such as bacteria, has a size of several hundreds of nanometers to several micrometers. The difference between the size of the stem cell colony and the size of the bacteria is an order unit. Therefore, the size of the observation target is distinguished to determine the presence of a different type of living body such as bacteria.

Specifically, the determination unit 31 compares a predetermined size threshold value with the size of the observation target in the observation image. When the number of observation targets with a size that is equal to or less than the size threshold value is equal to or greater than a predetermined threshold value, the determination unit 31 can determine that a different type of living body is included in the observation region. In this embodiment, the maximum length of the observation target is acquired as the size of the observation target. However, the invention is not limited thereto. For example, the average length of the observation target may be used as the size of the observation target.

When the shape of the observation target is acquired, the difference between the size of the stem cell colony and the size of the term is an order unit. Therefore, the shape of the observation target is distinguished to determine a different type of living body such as bacteria.

Specifically, the determination unit 31 performs, for example, edge detection to acquire the shape of the observation target in the observation image and performs pattern matching between a predetermined shape of bacteria and the shape of the observation target. When the number of observation targets having a shape similar to the shape of the bacteria is equal to or greater than a predetermined threshold value, the determination unit 31 can determine that a different type of living body is included in the observation region.

As described above, the difference between the size of the stem cell colony and the size of the bacteria is an order unit and the difference between the size of the nucleus of the stem cell colony, which is in the range of 10 μm to several tens of micrometers, and the size of the bacteria is also an order unit. Therefore, when the frequency characteristics of the observation target are acquired, the spatial frequency characteristics of the stem cell colony and the bacteria are acquired from the observation image and the acquired spatial frequency characteristics are distinguished to determine a different type of living body such as bacteria.

Specifically, the determination unit 31 performs, for example, a Fourier transform process on the observation image to acquire the spatial frequency characteristics of the observation target in the observation image. When a spectrum indicating an image component of the bacteria is present in the spatial frequency characteristics, the determination unit 31 can determine that a different type of living body is included in the observation region. Among a stem cell colony, the nucleus of the stem cell, and bacteria, a spectrum indicating an image component of the bacteria is the highest spatial frequency component. Therefore, the spectrum of the spatial frequency component is detected as the spatial frequency characteristics to determine whether bacteria are included in the observation region. In addition, when the spatial frequency characteristics of the observation image are acquired, processing, such as edge detection, may be performed.

Examples of the information about the change in the observation target over time include the amount of movement and the multiplication rate of the observation target. The determination unit 31 acquires at least one of them and determines whether a different type of living body is included in the observation region.

When the amount of movement of the observation target is acquired, for example, the stem cell colony moves on the culture medium in an order unit of a few hours to a few days while a different type of living body, such as bacteria, moves on the culture medium in an order unit of several microseconds which is close to that in a Brownian motion. The difference between the amount of movement of the stem cell colony and the amount of movement of the bacteria is an order unit. Therefore, the amount of movement of the observation target is distinguished to determine a different type of living body such as bacteria.

Specifically, the determination unit 31 acquires the amount of movement of the observation target between the observation images on the basis of a plurality of frames of observation images and compares the amount of movement of each observation target with a predetermined movement amount threshold value. When the observation target having the amount of movement that is equal to or greater than the movement amount threshold value is present in the observation image, the determination unit 31 can determine that a different type of living body is included in the observation region.

When the multiplication rate of the observation target is acquired, for example, the stem cell multiplies in the range of one day to two days while a different type of living body, such as bacteria, multiplies in a few tens of minutes. The difference between the multiplication rate of the stem cell and the multiplication rate of the bacteria is an order unit. Therefore, the multiplication rate of the observation target is distinguished to determine a different type of living body, such as bacteria.

Specifically, the determination unit 31 acquires a plurality of frames of observation images, detects a pattern, such as a black point having a concentration equal to or greater than a predetermined threshold value, in each observation image, and counts the number of detected patterns. The nucleus of the stem cell or a different type of living body, such as bacteria, is detected as the pattern. Therefore, the determination unit 31 acquires the difference between the count values of the numbers of patterns in the observation images, calculates the multiplication rate on the basis of the difference between the count values and the imaging interval of the observation image, and compares the calculated multiplication rate with a predetermined multiplication rate threshold value. When the difference between the count values is equal to or greater than the multiplication rate threshold value, the determination unit 31 can determine that a different type of living body is included in the observation region. In the above description, the multiplication rate is calculated. However, it may be determined whether the difference between the count values is equal to or greater than the threshold value, without calculating the multiplication rate.

When the determination of whether a different type of living body is included in the observation region ends, the determination unit 31 outputs the determination result to the display control unit 32.

In addition, when the determination of whether a different type of living body is included ends, the determination unit 31 outputs the end signal to the imaging device 2. When receiving the end signal which is output from the determination unit 31 as described above, the imaging device 2 performs the switching between the imaging intervals, between the magnifications, between the numbers of exposures (exposure times), or between the amounts of exposure.

The display control unit 32 acquires the observation image output from the observation image acquisition unit 30 and displays the observation image on the display 4. In addition, the display control unit 32 acquires the determination result output from the determination unit 31 and displays the determination result on the display 4.

When displaying the determination result on the display 4, the display control unit 32 may display various parameters used for the determination. Specifically, for example, when acquiring the form information of the observation target, the determination unit 31 may display, for example, the number of observation targets having a size equal to or less than the size threshold value, the number of observation targets having a shape similar to the shape of the bacteria detected by pattern matching, and the spatial frequency characteristics of the observation image on the display 4.

When acquiring the information about the change in the observation target over time, the determination unit 31 may display, for example, the amount of movement of the observation target which is equal to or greater than the movement amount threshold value, the number of patterns, such as black points, in each observation image, the difference between the count values of the patterns in the observation images, and the multiplication rate which is calculated on the basis of the difference between the count values on the display 4.

The input device 5 includes, for example, a mouse or a keyboard and receives an operation input by the user. In particular, in this embodiment, the input device 5 can receive the input of an instruction to switch the imaging interval at which the observation image is captured, the magnification of the optical system 20, the number of exposures (exposure time) in one imaging operation, or the amount of exposure.

Figure 2:
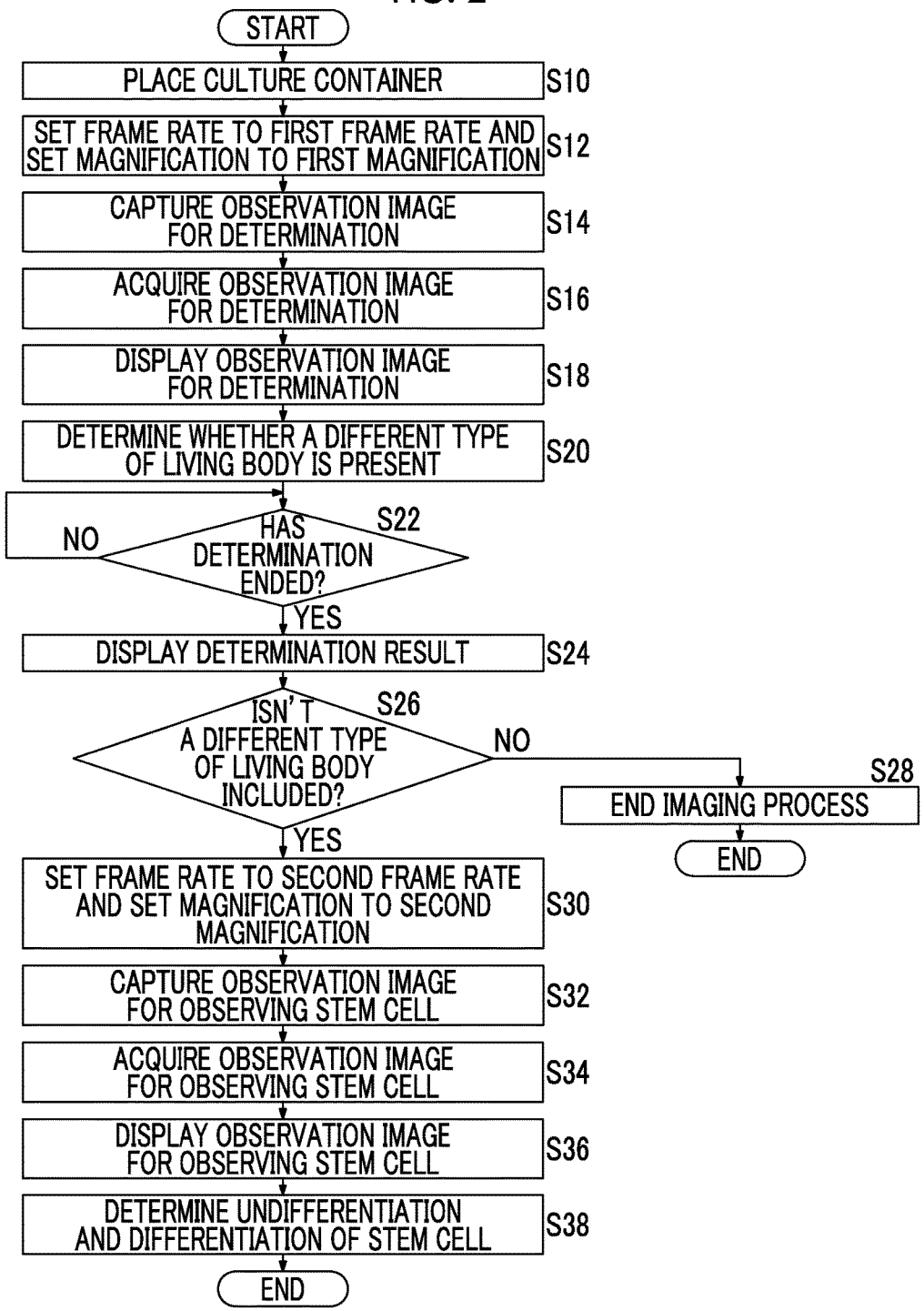
FIG. 2 is a flowchart illustrating the operation of the stem cell culture observation system illustrated in FIG. 1.

Next, the operation of the stem cell culture observation system will be described with reference to the flowchart illustrated in FIG. 2.

First, in the stem cell culture device 1, the transport unit 11 selects the culture container of which the image is to be captured from a plurality of culture containers provided in the cell culture device 1 and the selected culture container is placed on the stage 10 (S10).

Then, before the observation image of the culture container placed on the stage 10 is captured, the control unit 22 of the imaging device 2 sets the imaging interval of the imaging element 21 to the first imaging interval and sets the magnification of the optical system 20 to the first magnification (S12). In addition, the control unit 22 sets the number of exposures (exposure time) in one imaging operation or the amount of exposure.

Then, the imaging device 2 captures the observation image which is used to determine whether a different type of living body other than the stem cell is included in the culture medium in the culture container (S14).

The observation image captured by the imaging device 2 is output to the different-type-of-living-body determination device 3 and is acquired by the observation image acquisition unit 30 of the different-type-of-living-body determination device 3 (S16).

Figure 3:
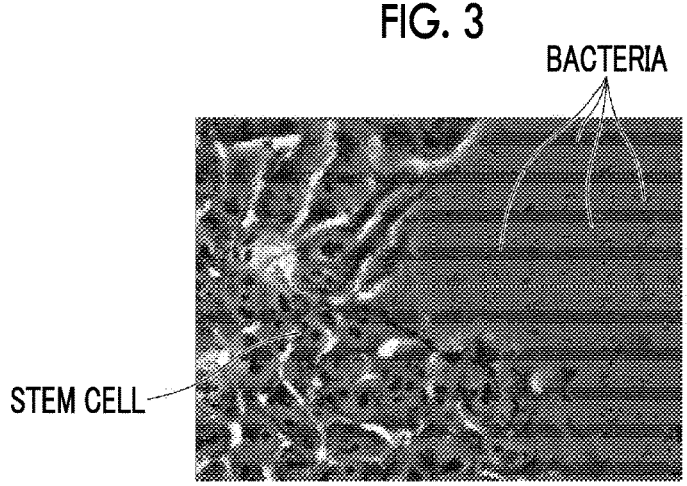
FIG. 3 is a diagram illustrating an example of an observation image in which bacteria as well as a stem cell are included in an observation region.
Figure 4:
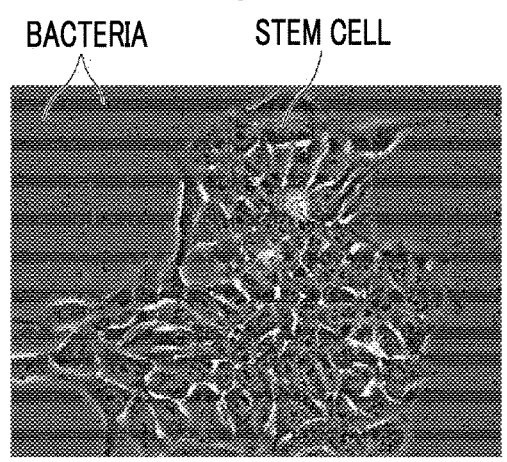
FIG. 4 is a diagram illustrating an example of an observation image in which bacteria as well as a stem cell are included in an observation region.
Figure 5:
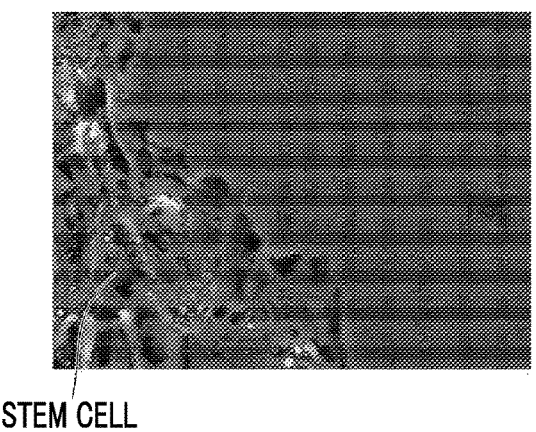
FIG. 5 is a diagram illustrating an example of an observation image in which a stem cell without any bacteria is included in an observation region.

The observation image acquired by the observation image acquisition unit 30 is output to the display control unit 32 and the display control unit 32 displays the observation image on the display 4 (S18). FIG. 3 is a diagram illustrating an example of an observation image in which bacteria as well as a stem cell are included in the observation region. The observation image illustrated in FIG. 3 is captured at the first magnification. FIG. 4 illustrates an observation image which is captured at the second magnification lower than the first magnification for comparison. In the observation image illustrated in FIG. 3, black points indicate bacteria which are present around the stem cell. FIG. 5 illustrates an example of an observation image in which no bacteria except the stem cell are included in the observation region. The observation image illustrated in FIG. 4 is also captured at the first magnification.

The observation image acquired by the observation image acquisition unit 30 is also output to the determination unit 31. As described above, the determination unit 31 acquires the form information of the observation region or the information about a change in the observation region over time from the observation image and determines whether a different type of living body other than the stem cell is included in the observation region on the basis of the information (S20).

When the determination process of the determination unit 31 ends (S22, YES), the determination result is output to the display control unit 32 and the display control unit 32 displays the determination result on the display 4 (S24).

When the determination result of the determination unit 31 shows that a different type of living body is included in the observation region (S26, NO), the determination unit 31 outputs a signal indicating the end of the imaging operation to the control unit 22 of the imaging device 2 and the control unit 22 ends the imaging operation in response to the input signal (S28).

On the other hand, when the determination result of the determination unit 31 shows that a different type of living body is not included in the observation region (S26, YES), the determination unit 31 outputs an end signal indicating that the determination process has ended to the control unit 22 of the imaging device 2. Then, the control unit 22 switches the imaging interval of the imaging element 21 from the first imaging interval to the second imaging interval and switches the magnification of the optical system 20 from the first magnification to the second magnification, in response to the input end signal (S30). In addition, in this case, the control unit 22 switches the number of exposures (exposure time) or the amount of exposure.

Then, the imaging device 2 captures the observation image used to observe the stem cell in detail (S32).

Figure 6:
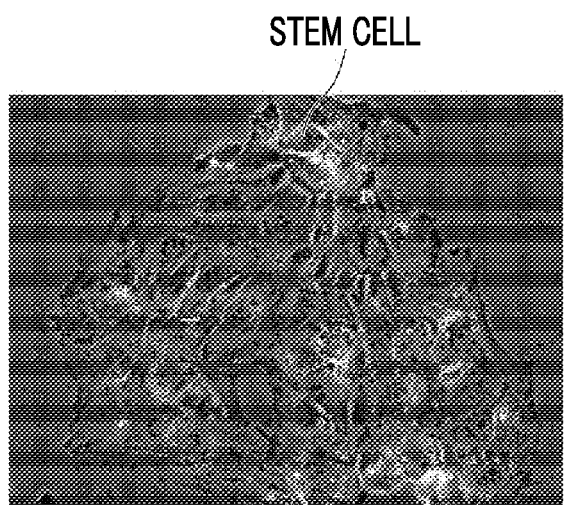
FIG. 6 is a diagram illustrating an example of an observation image in which no bacteria except a stem cell are included in an observation region.

The observation image captured by the imaging device 2 is output to the different-type-of-living-body determination device 3 and is acquired by the observation image acquisition unit 30 of the different-type-of-living-body determination device 3 (S34). The observation image acquired by the observation image acquisition unit 30 is output to the display control unit 32 and the display control unit 32 displays the observation image for observing the stem cell on the display 4 (S36). FIG. 6 illustrates an example of an observation image which is captured at the second magnification and in which a different type of living body is not included in the observation region.

Then, the differentiation and undifferentiation of the stem cell are determined on the basis of the observation image displayed on the display 4 (S38). The user may observe the observation image to determine the differentiation and undifferentiation of the stem cell or the differentiation and undifferentiation of the stem cell may be automatically determined using the observation image. Various known methods may be used as a method for automatically determining the differentiation and undifferentiation of the stem cell using the observation image. For example, a method for determining the differentiation and undifferentiation of the stem cell on the basis of the shape of a stem cell colony can be used.

The stem cell culture observation system according to the above-described embodiment captures the image of the observation region including the stem cell to acquire the observation image and determines whether a different type of living body is included in the observation region on the basis of at least one of the form information of the observation target and the information about a change in the observation target over time which are acquired from the acquired observation image. Therefore, it is possible to quickly detect the mixture of a different type of living body, such as bacteria, without adding, for example, a sample.

What is claimed is:

1. An observation image determination device comprising:
   a memory;
   an imaging device which captures an observation image; and
   a processor coupled to the memory and the processor configured to:
   capture an image of an observation region including a stem cell to be cultured to acquire the observation image; and
   determine whether a living body of a different type from the stem cell is included in the observation region,
   wherein whether the different type of living body is included in the observation region is determined on the basis of spatial frequency characteristics of an observation target acquired from the observation image and predetermined spatial frequency characteristics of the different type of living body,
   wherein the spatial frequency characteristics is a spectrum of a spatial frequency component, and
   wherein the imaging device is adjusted to determine whether the different types of living body is included in the captured observation image.

2. The observation image determination device according to claim 1,
   wherein the processor determines whether the different type of living body is included in the observation region on the basis of at least one of the size and shape of the observation target.

3. The observation image determination device according to claim 2,
   wherein, when the observation target having a size equal to or less than a predetermined size threshold value is present, the processor determines that the different type of living body is included in the observation region.

4. The observation image determination device according to claim 2,
   wherein the processor performs pattern matching between the shape of the observation target and a predetermined shape of the different type of living body to determine whether the different type of living body is included in the observation region.

5. The observation image determination device according to claim 1,
   wherein the processor determines whether the different type of living body is included in the observation region on the basis of at least one of an amount of movement of the observation target and a multiplication rate of the observation target.

6. The observation image determination device according to claim 5,
   wherein, when the amount of movement of the observation target is equal to or greater than a predetermined movement amount threshold value, the processor determines that the different type of living body is included in the observation region.

7. The observation image determination device according to claim 5,
   wherein, when the multiplication rate of the observation target is equal to or greater than a predetermined multiplication rate threshold value, the processor determines that the different type of living body is included in the observation region.

8. The observation image determination device according to claim 1,
   wherein the imaging device is configured to perform switching between a first imaging interval when the observation image used to determine whether the different type of living body is included is captured and a second imaging interval when the observation image used to observe the stem cell is captured, and
   wherein the first imaging interval is shorter than the second imaging interval.

9. The observation image determination device according to claim 8,
wherein the processor outputs an end signal to the imaging device when the determination of whether the different type of living body is included ends, and
the imaging device automatically switches the first imaging interval to the second imaging interval in response to the end signal.

10. The observation image determination device according to claim 1,
wherein the imaging device can perform switching between a first magnification when the observation image used to determine whether the different type of living body is included is captured and a second magnification when the observation image used to observe the stem cell is captured, and
the first magnification is higher than the second magnification.

11. The observation image determination device according to claim 10,
wherein the processor outputs an end signal to the imaging device when the determination of whether the different type of living body is included ends, and
the imaging device automatically switches the first magnification to the second magnification in response to the end signal.

12. The observation image determination device according to claim 1,
wherein the imaging device is configured to perform switching between a first exposure time when the observation image used to determine whether the different type of living body is included is captured and a second exposure time when the observation image used to observe the stem cell is captured, and
wherein the first exposure time is longer than the second exposure time.

13. The observation image determination device according to claim 12,
wherein the processor outputs an end signal to the imaging device when the determination of whether the different type of living body is included ends, and
wherein the imaging device automatically switches the first exposure time to the second exposure time in response to the end signal.

14. The observation image determination device according to claim 1,
wherein the imaging device can perform switching between a first amount of exposure when the observation image used to determine whether the different type of living body is included is captured and a second amount of exposure when the observation image used to observe the stem cell is captured, and
wherein the second amount of exposure is more than the first amount of exposure.

15. The observation image determination device according to claim 14,
wherein the processor outputs an end signal to the imaging device when the determination of whether the different type of living body is included ends, and
wherein the imaging device automatically switches the first amount of exposure to the second amount of exposure in response to the end signal.

16. An observation image determination method comprising:
capturing an image of an observation region including a stem cell to be cultured to acquire an observation image, wherein the observation image is captured by an imaging device; and
determining whether a living body of a different type from the stem cell is included in the observation region on the basis of spatial frequency characteristics of an observation target acquired from the observation image and predetermined spatial frequency characteristics of the different type of living body,
wherein the spatial frequency characteristics is a spectrum of a spatial frequency component, and
wherein the imaging device is adjusted to determine whether the different type of living body is included in the captured observation image.

17. A non-transitory computer-readable recording medium having stored therein an observation image determination program that causes a computer to function as:
an observation image acquisition unit that captures an image of an observation region including a stem cell to be cultured to acquire an observation image that is captured by an imaging device; and
a determination unit that determines whether a living body of a different type from the stem cell is included in the observation region,
wherein the determination unit determines whether the different type of living body is included in the observation region on the basis of spatial frequency characteristics of an observation target acquired from the observation image and predetermined spatial frequency characteristics of the different type of living body, and
wherein the spatial frequency characteristics is a spectrum of a spatial frequency component, and
wherein the imaging device is adjusted to determine, by the determination unit, whether the different type of living body is included in the captured observation image.

* * * * *